United States Patent
Lee et al.

(10) Patent No.: US 6,635,471 B1
(45) Date of Patent: *Oct. 21, 2003

(54) TEMPERATURE CONTROL OF INCUBATION VESSELS USING ELECTRICALLY CONDUCTING POLYMERS

(75) Inventors: Martin A Lee, Salisbury (GB); Dario L Leslie, Salisbury (GB); Paul Moore, Salisbury (GB)

(73) Assignee: The Secretary of State for Defence in Her Britannic Majesty's Government of the United Kingdom of Great Britain and Northern Ireland, Hampshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/700,757
(22) PCT Filed: May 17, 1999
(86) PCT No.: PCT/GB99/01553
   § 371 (c)(1),
   (2), (4) Date: Nov. 20, 2000
(87) PCT Pub. No.: WO99/61578
   PCT Pub. Date: Dec. 2, 1999

(30) Foreign Application Priority Data
May 23, 1998 (GB) .............................................. 9811060

(51) Int. Cl.$^7$ ................................................ C12M 1/02
(52) U.S. Cl. ..................... 435/303.1; 435/325; 435/243; 435/304.1; 435/305.2; 219/386; 219/428; 219/438
(58) Field of Search ........................... 435/303.1, 304.1, 435/809, 3, 243, 325, 304.3, 305.2; 422/99, 104, 102; 219/286, 438, 428; 359/395

(56) References Cited

U.S. PATENT DOCUMENTS

| 2,883,307 | A | * | 4/1959 | Orr, Jr. |
| 3,556,731 | A | * | 1/1971 | Martin |
| 5,382,382 | A | * | 1/1995 | Asakura et al. |
| 5,552,321 | A | | 9/1996 | Focht |
| 5,582,754 | A | * | 12/1996 | Smith et al. |
| 5,819,842 | A | * | 10/1998 | Potter et al. ................. 165/206 |
| 5,843,741 | A | * | 12/1998 | Wong et al. |
| 5,976,284 | A | * | 11/1999 | Calvert et al. ................. 156/51 |
| 6,095,148 | A | * | 8/2000 | Shastri et al. |
| 6,312,886 | B1 | * | 11/2001 | Lee et al. |
| 6,436,355 | B1 | * | 8/2002 | Lee et al. .................... 422/199 |

FOREIGN PATENT DOCUMENTS

| DE | 31 32 926 | | 7/1982 | |
| EP | 0 731 623 A2 | * | 9/1996 | |
| GB | 2 333 250 | | 7/1999 | |
| JP | 01090044 A | * | 4/1989 | ............. B01L/3/08 |
| WO | WO 98 24548 | | 6/1998 | |

* cited by examiner

Primary Examiner—William H. Beisner
(74) Attorney, Agent, or Firm—Nixon & Vanderhye P.C.

(57) ABSTRACT

The use of incubation means for the controlled heating of biological materials, said means comprising an electrically conducting polymer connectable to a power supply, said polymer being either contiguous or integral with an incubation vessel, or adapted to be in thermal contact with an incubation vessel. Incubation apparatus including such means and a method for culturing biological materials using them are also described and claimed.

16 Claims, 1 Drawing Sheet

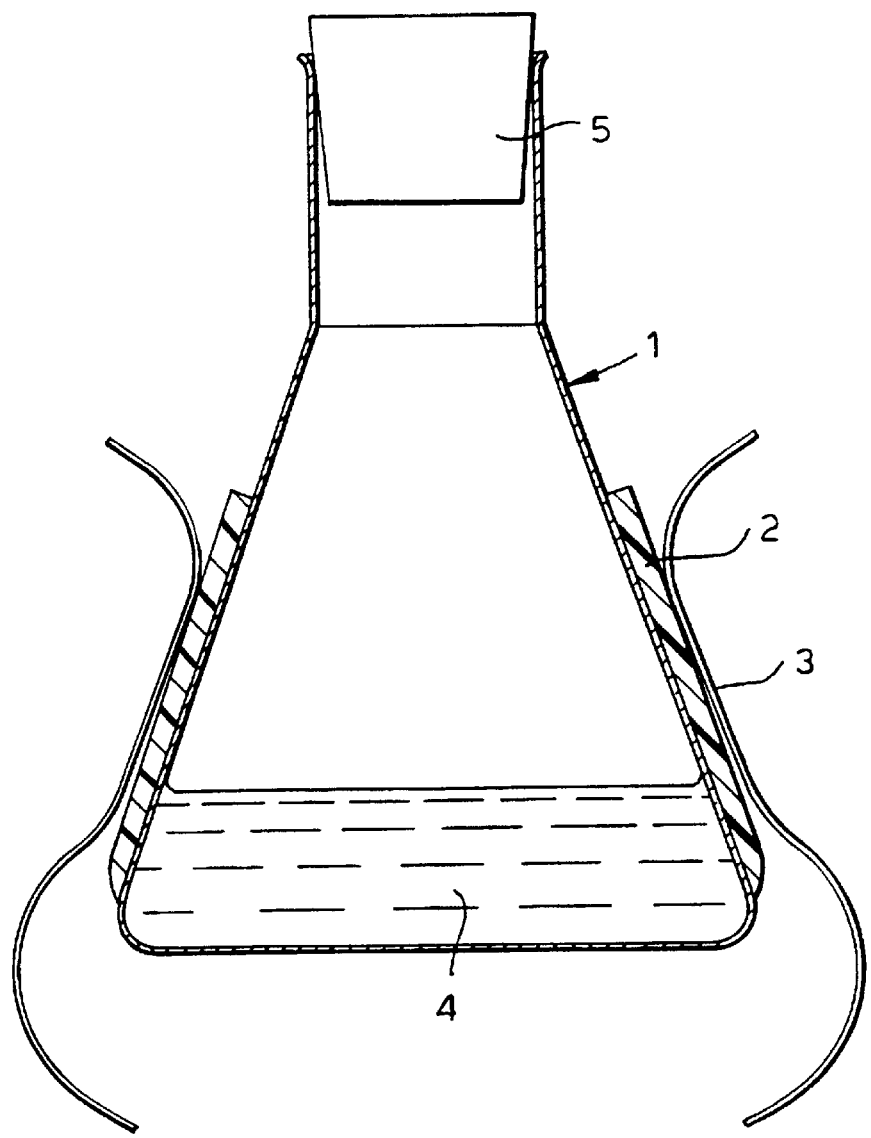

TEMPERATURE CONTROL OF INCUBATION VESSELS USING ELECTRICALLY CONDUCTING POLYMERS

The present invention relates to the use of electrically conducting polymers in the production of apparatus such as incubators for use in the culture of biological material as well as apparatus and methods for incubating biological material.

Culture of biological material, such as plant or animal cells, bacteria, viruses or hybridoma or other immortal cell lines are required in a wide variety of purposes. For example, the cell lines may be cultured for use in experimental purposes. In addition, bacteria and in particular recombinant bacteria may be cultured used in the production of materials such as antibiotics or other pharmaceuticals. Antibodies useful in diagnosis and therapy in a wide range of fields are prepared for example by the culture of hybridoma or other immortal cells lines.

For diagnostic purposes, for example in the areas of food hygiene monitoring, it may be necessary to culture any bacterial or viral strains isolated in order to obtain significant quantities for detection and/or identification.

Plant cells may be cultured to prepare calluses for use in transformation to produce recombinant plants.

The controlled heating of shake flasks or other vessels used in the culture of biological material is often carried out using large heaters or incubators. Multiple shake flasks, each containing the biological material to be tested and culture medium are held within these devices. The temperature within the incubator is held at a temperature at which the biological material may be grown. Generally, this will be of the order of 37° C. which is an acceptable temperature for the culture of many types of biological material. However, this may not be the optimum culture temperature for all biological material being cultured within the container, particularly when a wide range of different biological materials are contained within different individual shake flasks.

Furthermore, this may not provide an economical method of heating where only a small number of samples are required as it is necessary to heat and maintain the entire apparatus at the desired temperature, even when only a few samples are contained within it.

Finally, incubation of certain strains, in particular recombinant stains of bacteria etc. require specific temperature conditions and transitions in order to induce or "switch on" desired genes. Certain strains require culturing for a predetermined period at one temperature followed by adjustment of the temperature to a different level in order to obtain expression of a particular gene. At present, such a complex operation has to be carried out manually, which means that an operator has to be present at the particular moment when the temperature change is required, in order to remove the incubation vessel from the constant temperature environment, and heat or cool it as appropriate.

There is a need for a more controllable method of heating incubation vessels used in the culture of biological material. Copending International Patent Application No. PCT/GB97/03187 describes reaction vessels which utilise electrically conducting polymers as the heating means. It has been found that such vessels may be adapted for use in the incubation of biological material.

According to the present invention there is provided the use of incubation means for the controlled heating of biological materials, said means comprising an electrically conducting polymer connectable to a power supply, said polymer being either contiguous or integral with an incubation vessel, or adapted to be in thermal contact with an incubation vessel.

Electrically conducting polymers are known in the art and may be obtained from Caliente Systems Inc. of Newark, USA. Other examples of such polymers are disclosed for instance in U.S. Pat. No. 5,106,540 and U.S. Pat. No. 5,106,538. Many polymers, for example, polytetrafluoroethylene (PTFE) or polyethylene (PE) can be formed into electrically conducting polymers by inclusion of graphite in the polymer material.

Suitable conducting polymers can provide temperatures up to 300° C. and so are well able to be used in incubation processes where the range of temperatures is between 0° and 100° C., typically between 15° and 50° C.

Incubation vessels which may be used in the context of the invention are well known in the art. They may comprise shake flasks, petrie dishes, test tubes, chemostats, fermenters or slides including microscope slides.

An advantage of the invention over a known incubators or ovens is that the temperature within individual incubation vessels can be controlled independently of one another.

The heating rate achievable depends upon the precise nature of the polymer, the dimensions of polymer used and the amount of current applied. Preferably the polymer has a high resistivity for example in excess of 1000 ohm.cm. The temperature of the polymer can be readily controlled by controlling the amount of electric current passing through the polymer, allowing it to be held at a desired temperature for the desired amount of time. Furthermore, the rate of transition between temperatures can be readily controlled after calibration, by delivering an appropriate electrical current, for example under the control of a computer programme.

Suitably however, the temperature within each vessel may be set using for example a simple thermostat device which cuts off the current to the polymer if the temperature within the flask exceeds the desired temperature.

The thermal properties of an electrically conducting polymer and in particular it low thermal mass, will ensure that adjustments in the temperature will take place rapidly. If desired however, the incubation vessel may be subjected to artificial cooling to further increase the speed of cooling. Suitable cooling methods include forced air cooling, for example by use of fans, immersion in ice or water baths etc.

In addition, the use of polymer as the heating element in an incubation vessel will generally allow the apparatus to take a more compact form than existing incubators. This may be useful when carrying out culture processes in field conditions such as in the open air, on a river, on a factory floor or even in a small shop.

The incubation vessel may take the form of a reagent container such as a glass, plastics or silicon container, with electrically conducting polymer arranged in close proximity to the container. In one embodiment of the vessel, the polymer is provided as a sheath which fits around the incubation vessel, in thermal contact with the vessel. The sheath can either be provided as a shaped cover which is designed to fit snugly around an incubation vessel or it can be provided as a strip of film which can be wrapped around the incubation vessel and secured.

The polymer sheath arrangement means that close thermal contact is achievable between the sheath and the incubation vessel. This ensures that the vessel quickly reaches the desired temperature without the usual lag time arising from the insulating effect of the air layer between the incubation vessel and the heater. Furthermore, a polymer sheath can be used to adapt apparatus using pre-existing incubation vessels. In particular, a strip of flexible polymer film can be wrapped around an incubation vessel of various different sizes and shapes.

Where a sheath is employed it may be advantageous for it to be perforated or in some way reticulated. This may increase the flexibility of the polymer and can permit even readier access by a cooling medium if the polymer is not itself used to effect the cooling.

In another embodiment of the invention, the polymer is provided as an integral part of the incubation vessel. The incubation vessel may be made from the polymer by extrusion, injection moulding or similar techniques. Alternatively, the incubation vessel may be manufactured using a composite construction in which a layer of the conducting polymer is interposed between layers of the material from which the vessel is made or in which the internal or external surfaces of the incubation vessel is coated with the polymer, or again in which the vessel is basically made of the polymer coated with a thin laminate of a culture medium compatible material. Such vessels may be produced using lamination and/or deposition such as chemical or electrochemical deposition techniques as is conventional in the art.

Vessels which comprise the polymer as an integral part may provide particularly compact structures.

If several incubation vessels are required for a particular reaction, any electrical connection points can be positioned so that a single supply can be connected to all the incubation vessels or tubes. The incubation vessels may be provided in an array.

Alternatively, each of or each group of incubation vessels may have its own heating profile set by adjusting the applied current to that vessel or group of vessels. This provides a further and particularly important advantage of incubation vessels with polymer in accordance with the invention over conventional incubators, in that the temperature of individual vessels can be controlled independently of one another. This means that each incubation vessel may be provided with its own thermal profile which may be optimised for the culture of the particular biological strain contained therein.

The polymer may suitably be provided in the form of a sheet material or film, for example of from 0.01 mm to 10 mm, such as from 1 to 10 mm, and preferably 0.1 to 0.3 mm thick. By using thin films, the volume of polymer required to cover a particular incubation vessel or surface is minimised. This reduces the time taken for the polymer to heat to the required temperature as the heat produced by passing the current through the polymer does not have to be distributed throughout a large volume of polymer material.

In use, the polymer component of the incubation vessel is arranged such that an electric current can be generated within the polymer. This can either be achieved by providing the polymer with connection points for connection to an electrical supply or by inducing an electric current within the polymer, for example by exposing the polymer to suitable electrical or magnetic fields.

Close thermal contact between the polymer and the incubation vessel is economical in that it does not require the heating of all the space within the incubator.

A particularly suitable incubation vessel for use in the context of the invention is a conical flask. The flask may either be surrounded by a sheath of conducting polymer. The sheath may be held in place by fixing means such as resilient clips. The clips are suitably of metal or other conducting material, as these may then act as the connection to the power supply.

Alternatively, the polymer may be integral with the flask. For example, the flask may contain a laminated form of polymer on glass or silicon.

In a different embodiment, the vessel may comprise a flat support plate such as a two-dimensional array in particular a chip such as a silicon wafer chip; or a slide, in particular a microscope slide, on which biological material and culture medium may be supported. The plate may be made from the polymer or the polymer may be provided as an integral part of the plate, either as a coating on one side of the plate or as a polymer layer within a composite construction as previously described.

Other suitable incubation vessel are tubes and cuvettes, which are known in the art.

Novel forms of incubation means for use in the invention as well as incubation vessels including these means form a further aspect of the invention.

The invention further provides incubation apparatus for the culture of biological material, said apparatus comprising an incubation vessel, an electrically conducting polymer which is either contiguous or integral with the incubation vessel, or positioned in thermal contact with the incubation vessel, a means for generating an electrical current within the electrically conducting polymer and a means for controlling the temperature within the incubation vessel.

The control means is suitably an automatic control means such as a thermostat device as are well known in the art, or a computer controlled interface arrangement. The latter may include a temperature monitoring device such as a thermocouple, which monitors the temperature of the incubation vessel and feeds this information into the control system so that the desired regime of heating and/or cooling is adhered to.

Alternatively, the temperature of the polymer may be monitored directly by measuring its resistivity, for example by arranging the polymer heating element as a resistor in a wheatstone bridge circuit arrangement. This avoids the use of other temperature measurement devices such as thermocouples.

Optionally, the apparatus further comprises artificial cooling means such as one or more fans.

The apparatus may include a plurality of incubation vessels. The polymer may be provided as an integral part of each container, as a sheath around each container or arranged such that a layer of polymer is interposed between adjacent containers. Any electrical connection points on the polymer may be connected to a single electrical supply, if a number of reactions requiring the same temperature stages are being carried out.

However, in a preferred embodiment the apparatus is arranged such that the polymer in contact with (or forming) a vessel or a group of vessels is connected to an individual supply, several vessels or groups of vessels being connected to different, independently controlled electrical supplies. With this arrangement, a number of different cultures requiring different temperatures or temperature stages can be carried out at the same time as each container or group of containers has its own heating element. This arrangement allows users to carry out a number of small batch cultures using a single vessels economically.

Where the incubation vessel comprises a slide or chip, the apparatus may comprise the slide or chip, an electrical supply, means for connecting the electrical supply to the slide or chip or for inducing an electrical current in the polymer and a means for controlling the current passing through the polymer layer in the slide or chip.

Incubation vessels and apparatus of the invention can be used in a variety of situations where biological material is required to be cultured. Thus the invention further provides a method of culturing a biological material which method comprises placing the biological material and a culture medium in an incubation vessel which is provided with incubation means as described above, and supplying a current to the incubation means so as to cause the incubation vessel to reach a predetermined temperature.

Embodiments of the present invention will now be described, by way of example, with reference to the accompanying drawing, wich is a diagram showing an embodiment of incubation apparatus of the invention.

In the drawing, a conical flask 1 is surrounded with a sheath of electrically conducting polymer 2. The polymer sheath 2 is held in place by means of a resilient metal clip 3. An electrical power supply (not shown) is connected to the clip 3.

In use, biological material in culture medium 4 is placed within the incubation vessel 1 which is stoppered by means of a bung 5. The sheath 2 is in close thermal contact with the incubation vessel 1. Electrical power is supplied to the clip 3 such that current is passed through the polymer sheath 2, thereby heating it and biological material inside the incubation vessel 1.

The electrical power supply is under the control of a thermostat device (not shown) which has been set to ensure that the temperature within the incubation vessel remains optimum for the particular condition or conditions under which the biological material grows.

The vessel 1 may, during the course of the reaction, be agitated or shaken, for example in a shaking apparatus as is well known in the art. Alternatively or additionally, the vessel may be is otherwise aerated for example by sparging. Depending upon the nature of the biological material being cultured, it may be necessary or desirable to effect the process in non-aerobic conditions, for example under a nitrogen atmosphere.

Although the vessel illustrated in the FIGURE comprises a conical flask, it will be appreciated that other forms of vessel including tubes, slides and dishes can be employed. The formation of the polymer will be adapted accordingly.

What is claimed is:

1. An incubation chamber for the culture of biological materials comprising an incubation vessel and heating means comprising an electrically conducting polymer connectable to an electrical supply, and control means for controlling the supply of current to the heating means, said control means being programmed to maintain a culture temperature within the incubation vessel.

2. Incubation apparatus for the culture of biological material, said apparatus comprising an incubation vessel, an electrically conducting polymer which is either contiguous or integral with the incubation vessel, or positioned in thermal contact with the incubation vessel, a means for generating an electrical current within the electrically conducting polymer and a means for controlling the electrical current within the electrically conducting polymer so as to maintain a culture temperature within the incubation vessel.

3. Apparatus as claimed in claim 2 and incorporating a plurality of incubation vessels at least some of which are supplied with electrically conducting polymer.

4. Apparatus as claimed in claim 3 and wherein the control means is arranged for the supply of current for a different temperature profile for various of the incubation vessels.

5. A method of culturing a biological material which method comprises:

(a) placing the biological material and a culture medium in an incubation vessel which has an electrically conducting polymer that is either contiguous, integral or in thermal contact with the incubation vessel, and (b) supplying a current to the electrically conducting polymer so as to cause the incubation vessel to reach and maintain a predetermined temperature so as to cause culture of the biological material.

6. A method according to claim 5 wherein biological material within a plurality of incubation vessels is incubated simultaneously.

7. A method according to claim 6 wherein each incubation vessel is heated individually to the temperature required for the culture taking place within that vessel.

8. A method according to claim 5 wherein the polymer of the incubation means is contiguous with an incubation vessel.

9. A method as claimed in claim 5 wherein the polymer of the incubation means forms a sheath around an incubation vessel.

10. A method as claimed in claim 9 wherein the sheath is integral with an incubation vessel.

11. A method as claimed in claim 5 wherein the polymer is in the form of a film.

12. A method as claimed in claim 5 and wherein the polymer is perforated or reticulated.

13. A method as claimed in claim 5 wherein the polymer forms a container for the biological material.

14. A method as claimed in claim 5 wherein an incubation vessel for biological material is provided and wherein one of the surfaces of the vessel is coated with the said polymer.

15. A method as claimed in claim 5 wherein the incubation vessel comprises a flask, dish or slide.

16. A method as claimed in claim 15 wherein the incubation vessel comprises a flask.

* * * * *